(12) United States Patent
Cattani

(10) Patent No.: US 9,625,375 B2
(45) Date of Patent: Apr. 18, 2017

(54) INSTRUMENT FOR MEASURING THE CONCENTRATION OF WATER ISOTOPES IN A GAS SAMPLE LOADED WITH WATER VAPOUR

(71) Applicant: Commissariat a l'energie atomique et aux energies alternatives, Paris (FR)

(72) Inventor: Olivier Cattani, Saint André les Vergers (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/408,858

(22) PCT Filed: Feb. 11, 2014

(86) PCT No.: PCT/EP2014/052637
§ 371 (c)(1),
(2) Date: Dec. 17, 2014

(87) PCT Pub. No.: WO2014/124934
PCT Pub. Date: Aug. 21, 2014

(65) Prior Publication Data
US 2015/0330895 A1    Nov. 19, 2015

(30) Foreign Application Priority Data

Feb. 12, 2013   (FR) ...................................... 13 51175
Feb. 10, 2014   (FR) ...................................... 14 51019

(51) Int. Cl.
*G01J 5/02*    (2006.01)
*G01N 21/3554*    (2014.01)
(Continued)

(52) U.S. Cl.
CPC ..... *G01N 21/3554* (2013.01); *G01N 21/3504* (2013.01); *G01N 33/0006* (2013.01); *G01N 2201/0612* (2013.01)

(58) Field of Classification Search
CPC .. G01N 21/3504; G01N 21/37; G01N 21/314; G01N 21/35; G01N 21/05
See application file for complete search history.

(56) References Cited

U.S. PATENT DOCUMENTS 4,708,013 A * 11/1987 Landis ................... G01N 30/06
73/23.24

OTHER PUBLICATIONS

Aemisegger et al. "Measuring variations of 18O and 2H in atmospheric water vapour using laser spectroscopy: an instrument characterisation study", Atmospheric Measurement Techniques Discussions, vol. 5, Feb. 15, 2012 (Feb. 15, 2012), pp. 1597-1655, DOI: 10.5194/amtd-5-1597-2012.*

(Continued)

*Primary Examiner* — David Porta
*Assistant Examiner* — Mamadou Faye
(74) *Attorney, Agent, or Firm* — Pillsbury Winthrop Shaw Pittman LLP

(57) ABSTRACT

An instrument for measuring the concentration of water isotopes in a gas sample loaded with water vapor, includes an analyzer; a vaporizer including a circuit that connects to the analyzer to transmit a vaporized calibration liquid to the analyzer and an output circuit for discharging the overflow of the vaporized calibration liquid, the output circuit arranged such that the overflow is discharged without passing through the analyzer and a purge circuit connected to the input of the vaporizer for sucking said vaporized purge fluid through the vaporizer during a purge operation, the purge circuit arranged such that the vaporized purge fluid does not pass through the analyzer; a selector for selectively establishing a first state establishing the circulation of the cali- (Continued)

bration liquid through the connection circuit and the circulation of the overflow through the output circuit and a second state establishing the circulation of the purge liquid through the purge circuit.

11 Claims, 2 Drawing Sheets

(51) Int. Cl.
*G01N 21/3504* (2014.01)
*G01N 33/00* (2006.01)

(56) References Cited

OTHER PUBLICATIONS

F. Aemisegger et al., "Measuring variations of $\sigma^{18}O$ and $\sigma^{2}H$ in atmospheric water vapour using laser spectroscopy: an instrument characterisation study," Atmospheric Measurement Techniques Discussions, vol. 5, Feb. 15, 2012, pp. 1597-1655.

X.-F. Wen et al., "Continuous measurement of water vapour D/H and $^{18}O/^{16}O$ isotope ratios in the atmosphere," Journal of Hydrology (2008), vol. 349, pp. 489-500.

International Search Report issued in International Patent Application No. PCT/EP2014/052637, dated Apr. 30, 2014.

\* cited by examiner

INSTRUMENT FOR MEASURING THE CONCENTRATION OF WATER ISOTOPES IN A GAS SAMPLE LOADED WITH WATER VAPOUR

CROSS REFERENCE TO RELATED APPLICATIONS

This application is the U.S. National Stage of PCT/EP2014/052637, filed Feb. 11, 2014, which in turn claims priority to French Patent Application No. 1351175, filed Feb. 12, 2013 and French Patent Application No. 1451019, filed Feb. 10, 2014, the entire contents of all applications are incorporated herein by reference in their entireties.

The present invention relates to an instrument for the measurement of isotopes in a gas sample.

The study of atmospheric water isotopes makes it possible to monitor cloud masses and in particular can provide information on the origin of the latter as well as on their histories (condensations, re-evaporation, etc.).

In order to continuously monitor the water isotopes contained in atmospheric water vapour, it is possible to use laser-diode spectrometers, which exploit the absorption of water molecules in the near infrared. One of the advantages of these instruments, particularly on account of their small size, is that they can be deployed outside of a dedicated analytical laboratory, and operate continuously.

These instruments, from the moment that they are in operation, continuously measure the relative humidity of an air flow pumped via an inlet, as well as the hydrogen and oxygen isotopic ratios.

It is necessary to be able to calibrate these instruments regularly, in order to be able to obtain reliable data.

The calibration consists in introducing, one after the other, two reference liquid samples constituted of water, the absolute isotopic values of which are perfectly determined, chosen so that they are both not too distant from each other, while encompassing the values of the samples to be analysed. The values then measured by the instrument make it possible to determine a calibration line for the instrument and thus to be able then to transform the measured values into absolute values.

The instrument is equipped with a vaporiser that makes it possible to transform the water of the reference samples into vapour phase and to measure them like any air sample.

The system enabling the calibration is called "Standard Delivery Module (S.D.M.)" and is composed of two syringes each connected, on the one hand, to an ampoule containing the corresponding reference sample and, on the other hand, via an injection nipple, to the vaporiser, itself connected to the analyser.

During a calibration phase, one of the syringes sucks, via the tubings, an amount corresponding to a predefined volume (for example 250 microliters) and distributes it very slowly to the analyser via the vaporiser, and the analyser measures throughout this time (which lasts for example for around 30 minutes) this reference sample. This step is then renewed with the other syringe.

Repeated calibrations at regular intervals make it possible in particular to be free of drift over time of the instrument; depending on the working conditions, this can range from several hours to a day.

On account of the use of very small volumes of reference samples, the tubings used typically have an external diameter of 1/16" and the internal diameter thereof does not exceed 0.20 mm; furthermore, the system does not remain under continuous pressure during the period of non-use, which inevitably leads to the appearance of air microbubbles in the tubings.

These bubbles, when they are introduced into the instrument during a calibration, perturb the analyses.

In order to avoid these perturbations being able to impair the continuous obtainment of accurate data, it is necessary to purge all of the tubings of the S.D.M., in order to be certain not to have bubbles in the circuit, before any calibration.

It is advisable when carrying out the purge to disconnect the tubings coming from the syringes at the level of the vaporiser and to purge the entire exterior of the instrument, in order to avoid any humidity saturation of the latter; once purged, the tubings are reconnected to the system and the calibration may be launched manually.

It should be noted that when the instrument is no longer used in the laboratory but deployed on a more or less isolated site, with a non-permanent human presence, it would be useful to be able to carry out the calibrations remotely, and thus to be able to purge the system remotely.

The invention aims to propose an instrument making it possible to carry out a purge of the tubings serving for the calibration, without human intervention and remotely.

In this context, the invention aims to provide an instrument for measuring the concentration of water isotopes in a gas sample loaded with water vapour, comprising:
at least one inlet tubing for receiving a purge liquid or a calibration liquid;
an analyser comprising:
an inlet for receiving a gas sample loaded with water vapour;
means of analysing said gas sample;
an outlet for discharging said gas sample loaded with water vapour after the measurement by the analysis means;
a connection circuit in normal measurement operation mode connecting the input to the output via said analysis means;
a vaporiser comprising:
at least one inlet connected to said inlet tubing;
means for vaporising said purge liquid or said calibration liquid;
a circuit that connects to the analyser in order to transmit said vaporised calibration liquid to the analyser, said circuit that connects to the analyser connecting the input of the vaporiser to the output of the analyser via said analysis means;
an output circuit for discharging the overflow of said calibration liquid vaporised during the measurement by the analyser, said output circuit being arranged such that the overflow is discharged without passing through the analyser;
a purge circuit connected to the input of the vaporiser for sucking said vaporised purge fluid through the vaporiser during a purge operation, said purge circuit being arranged such that said vaporised purge fluid does not pass through the analyser;
means for selectively establishing:
a first state, known as calibration operation state, establishing the circulation of the calibration liquid through the circuit that connects to the analyser and the circulation of the overflow of the vaporised calibration liquid through the output circuit of the vaporiser;
a second state, known as purge operation state, establishing the circulation of the purge liquid through the purge circuit.

Thanks to the invention, advantageously two states of the instrument are used, corresponding to:

a state of purge of the tubing (it being understood that the instrument generally comprises two tubings for which this purge may be carried out successively) which can be carried out automatically without altering the accuracy of the measurements of the analyser. It is no longer necessary to disconnect the tubings conveying the reference samples, as is known in the prior art. Furthermore, thanks to the arrangement according to the invention, the analyser is short-circuited such that the purge liquid does not pass through the analyser when it is used to purge the tubing. Put another way, the flow discharged from the vaporiser is deviated without this flow passing through the analyser. Thus, the purge liquid does not risk damaging by immersion the analysis means (typically an infrared absorption spectrometer) comprised in the analyser. This rapid and automatic purge moreover makes it possible to avoid water saturation during following measurements and to dry the fluid circuit rapidly without interrupting the use of the analyser for too long a time; to carry out the purge, the purge liquids are sent via the inlet tubings into the vaporiser, where they are vaporised, then are discharged via the purge circuit. The amount of liquid thereby discharged is chosen so as to replace the volume of liquid initially present in the tubings, potentially loaded with air bubbles, by liquid free of air bubbles, coming from the tank containing the reference sample and withdrawn at the moment of the purge operation. It will finally be noted that the operation in purge mode makes it possible to continue to carry out measurements by the analyser in normal operation (i.e. via its inlet on which it receives a gas sample loaded with water vapour, said gas passing through the analysis means and being discharged via the output of the analyser);

a calibration operation state during which the calibration liquid vaporised by the vaporiser penetrates into the analyser to be analysed and serves for the calibration; in this state, moreover, the output circuit of the vaporiser is kept open (for example to the open air) so as to evacuate the overflow of liquid present in the vaporiser and which could be introduced into the analyser.

The instrument according to the invention may also have one or more of the following characteristics, considered individually or according to all technically possible combinations thereof:

the circulation of the gas sample loaded with water vapour through the connection circuit of the analyser is established during said second state;

said selective establishment means comprise a first valve in the output circuit of the vaporiser and a second valve in the purge circuit, the first valve being open in the first state and closed in the second state, the second valve being open in the second state and closed in the first state;

said valves are electrically operated valves controlled by a control circuit;

the purge circuit comprises a pump;

the purge circuit comprises a desiccator upstream of the pump;

the second valve is arranged upstream of the pump;

the escape of the vaporised calibration liquid from the output circuit takes place to the open air;

the instrument according to the invention comprises two inlet tubings, each being adapted to receive a purge liquid or a calibration liquid, said vaporiser comprising two inlets connected respectively to one of said inlet tubings;

the instrument according to the invention comprises software means to assure the remote or automatic control of said means for selectively establishing said first and second states.

Other characteristics and advantages of the invention will become clear from the description that is given thereof hereafter, for indicative purposes and in no way limiting, with reference to the appended figures, among which:

The circulations of fluid in the different fluid circuits according to the different states (FIGS. 1 to 3) of the instrument according to the invention are represented in heavy line compared to non-active circuits.

Figure 1:
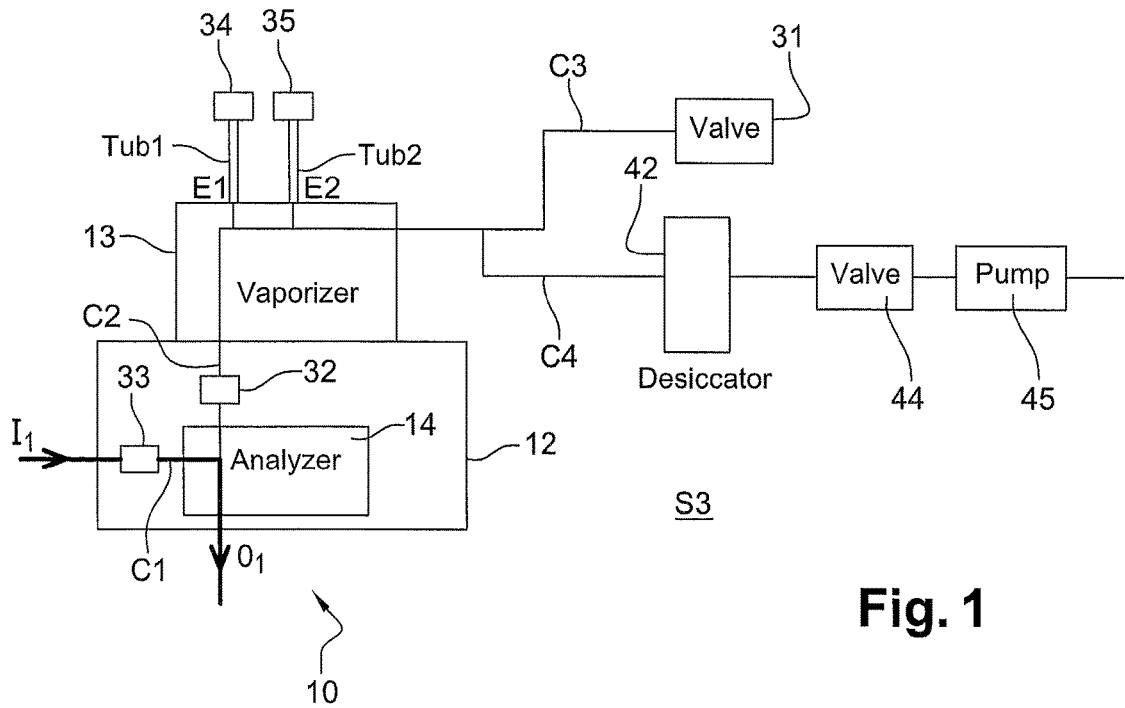
FIGS. 1 to 3 represent a measuring instrument according to the invention according to three states of operation in normal operation mode, in calibration mode and in purge mode.
Figure 2:
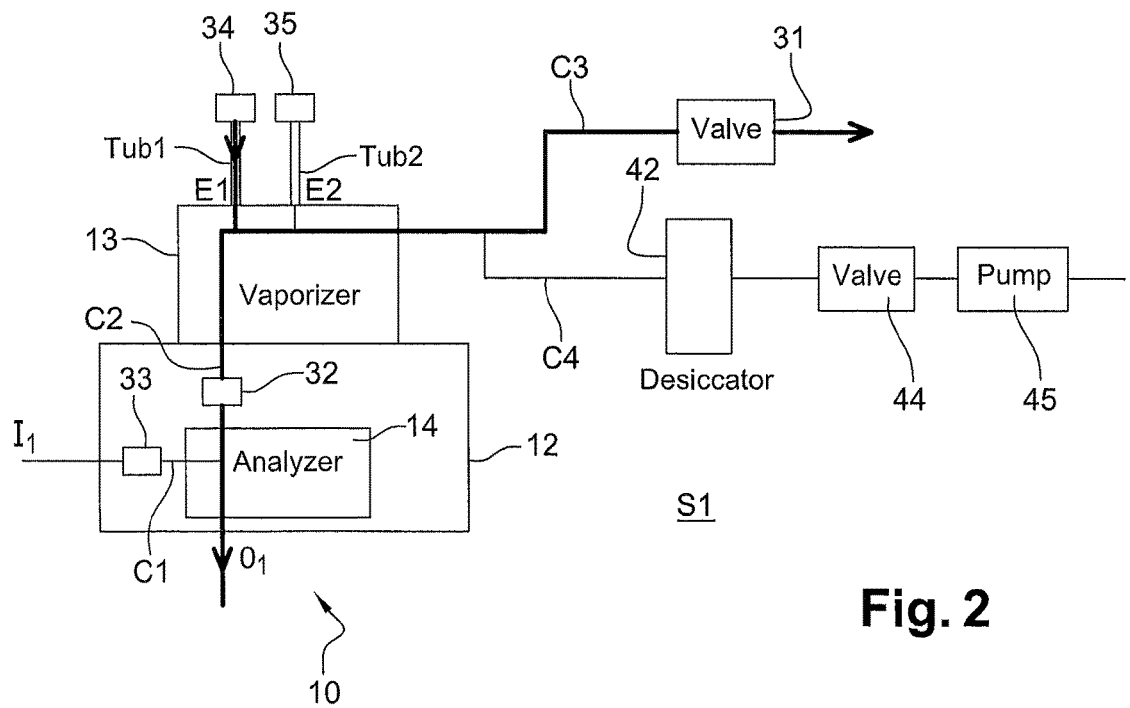
Figure 3:
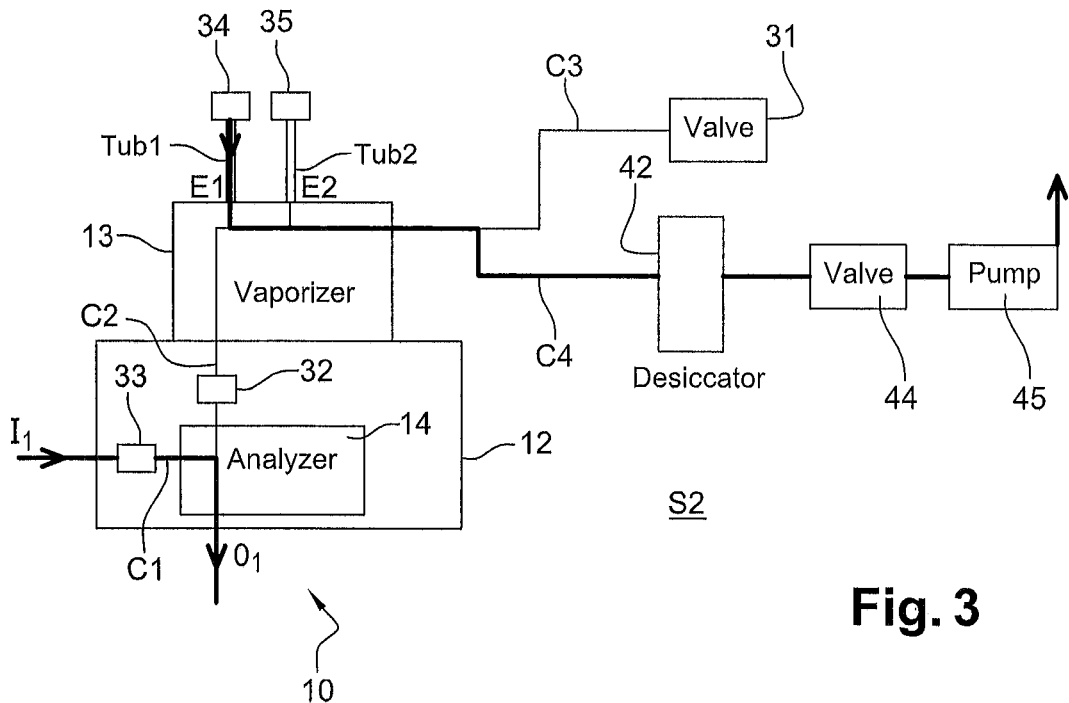

The measuring instrument 10 according to the invention represented in FIGS. 1 to 3 comprises:

a vaporiser 13 able to receive two calibration liquids via two inlets E1 and E2 connected respectively to two tubings Tub1 and Tub2;

an analyser 12, supplied by the vaporiser 13.

The measuring instrument 10 uses the system enabling calibration known as "Standard. Delivery Module (S.D.M.)" and comprises two syringes 34 and 35 each connected to an ampoule (not shown) containing a reference sample; these syringes 34 and 35 are advantageously motorised in order to be able to be controlled remotely and are connected respectively to the tubings Tub1 and Tub2.

The analyser includes analysis means 14 formed for example of an infrared absorption spectrometer using laser diodes. The analyser is for example an analyser bearing the trade name PICARRO LTub130-i.

A person skilled in the art knows the normal operation S3 of the analyser 12, illustrated in FIG. 1. The latter comprises an inlet I1 for receiving the sample of air to be analysed and an outlet O1 for discharging said sample. A connection circuit C1 is established between the input I1 and the output O1, said circuit assuring the passage of the sample via the analysis means 14.

The vaporiser 13 makes it possible to transform the water of the reference samples into vapour phase received on one of the inlets E1 or E2 thereof via one of the tubings Tub1 or Tub2 and to measure them like any air sample.

The vaporiser 13 according to the invention further comprises:

a circuit C2 that connects to the analyser 10;

an output circuit C3;

a purge circuit C4.

The input E1 (and the input E2) of the vaporiser communicate with the connection circuit C2, the output circuit C3 and the purge circuit C4.

The output circuit C3 comprises a valve 31, normally open, the output of which is to the open air.

The purge circuit C4 comprises a desiccator 42, a valve normally closed 44 and a pump 45, the output of which is to the open air.

The desiccator 42 arranged upstream of the pump 45 makes it possible not to damage the latter through water saturation, and comprises for example a desiccant cartridge for example of wick type 8 with coloured indicator, for example from the W.H. HAMMOND DRIERITE COMPANY.

The pump 45 is preferentially a membrane type pump such as the pump sold under the reference KNF N86KN.18.

The valves 31 and 44 are for example electrically operated 2-way valves (normally open NO or normally closed NF) having the reference 21A2ZV55G, supplied by the firm ODE France; the body of these valves is made of brass, with a passage diameter of the order of 5.5 mm; they have been chosen for their low cost and their great reliability in heating systems (the implementation of the vaporiser indeed leading to a heating up of the liquids).

Figure 4:
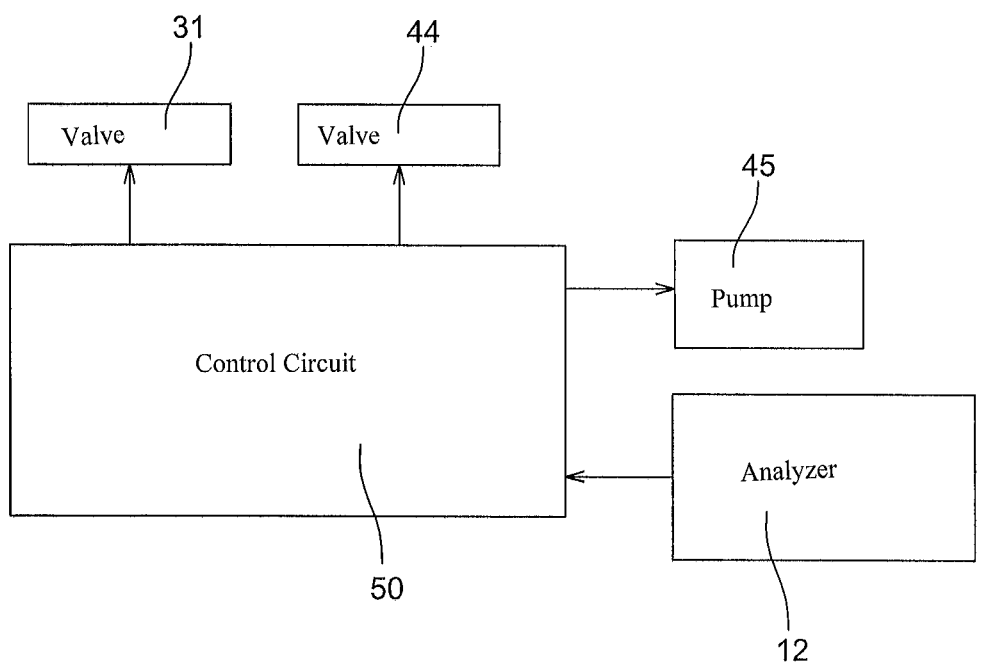
FIG. 4 represents an example of circuit for controlling the instrument of FIG. 1.

The valves 31 and 44 are for example electrically operated valves controlled by a control circuit 50, represented schematically in FIG. 4 and which can be incorporated in the instrument 10 according to the invention. This control circuit 50 comprises software means enabling the control of said valves 31 and 44.

The control circuit 50 can also control the operation of the pump 45.

FIG. 2 represents the state S1 of operation of the instrument 10 according to the invention in calibration mode (designated indifferently by the term calibration).

In this state S1, the valve 31 of the circuit C3 is open and the valve 44 of the circuit C4 is closed A calibration liquid is injected via the tubing Tub1, enters into the vaporiser 13 via the input E1 then is vaporised by the vaporiser 13. The vaporised liquid then follows the circuit C2, which allows it to pass from the vaporiser 13 to the analyser 12 and to be analysed by the analysis means 14, to be discharged via the output O1. In parallel, since the valve 31 is open, the overflow of vaporised liquid that does not penetrate into the analyser 12 is discharged via the output circuit C3 to the open air.

The operation is repeated on the tubing Tub2.

In the state S1, the connection circuit C1 is not active (i.e. the connection circuit is interrupted). For this, the instrument 10 according to the invention comprises for example a valve 33 making it possible to isolate the input I1 from the analysis means 14.

FIG. 3 represents the state S2 of operation of the instrument 10 according to the invention in purge mode.

In this state S2, the valve 31 of the circuit C3 is closed and the valve 44 of the circuit C4 is open.

In order to purge the instrument according to the invention before the calibration phase, the valve 31 is closed and the valve 44 is opened and the pump 45 is started up. Into inlet E1 is injected one of the reference liquids (that will serve as purge liquid) coming from the tubing Tub1 into the vaporiser 13 and the gas produced by the vaporisation of this liquid is sucked up by the pump 45. Then this purge action is reiterated with the other reference liquid injected via the tubing Tub2. In this state S2, there is no connection between the vaporiser 13 and the analysis means 14; put another way, no fluid circulates in the circuit C2 represented in FIG. 2 (in the same way as no fluid circulates in the circuit C4). In order to interrupt the circuit C2, the instrument 10 according to the invention comprises for example a valve 32 between the vaporiser and the analysis means 14. The circuit C2 connecting the vaporiser to the analyser is thereby interrupted.

It will be noted that the valves 32 and 33 may advantageously be replaced by a three-way valve (i.e. a valve making it possible, via a "Y" connection, to connect the output O1 of the analyser respectively to the circuit C1 or the circuit C2).

The amount of liquid, sufficient for discharging the bubbles present in the tubings Tub1 or Tub2, is advantageously the total volume of the syringes.

Once the two amounts have been evaporated and discharged, it is possible to return to the state S1 and to carry out successively the measurement of the water vapour coming from the vaporisation of the calibration liquids by closing the valve 44, while interrupting the operation of the pump 45 and by opening the valve 31.

From these two measurements, the calibration line is calculated, and it is then possible to carry out the measurement of the isotopes of the water vapour contained in the gas sample.

It will be noted that, in the state S2 (operation in purge mode), it is entirely possible to use the analyser 12 in normal operation mode (that is to say by activating the connection circuit C1.

Via the control circuit 50 of FIG. 4, the analyser 12 executes sequentially and automatically, for example by means of software, all of the steps necessary for the purge before a new calibration.

The instrument 10 may also be arranged to enable a remote maintenance intervention, for example thanks to free available software such as Teamviewer or Log Me In. This allows the user to retake control of actions during automatic routine measurements. He can then trigger the start-up of the system by using a functionality of the software of the analyser, making it possible to control the valves of the analyser, this software being for example that known under the reference External Valve Sequencer of the firm PICARRO.

The control circuit 50 is for example connected to an outlet route of the analyser, making it possible to send to the control circuit 50 an order for switching over the valves 31, 32, 33 and 44, as well as the start-up of the extraction pump 45, which takes place simultaneously with the closing of the valve 31 of the output circuit C3 and with the opening of the valve 42 of the purge circuit C4 or of operation of the motorised syringes 34 or 35.

Thanks to the invention, the purge can take place automatically and rapidly, as often as necessary.

The invention is not limited to the example illustrated. In particular, the valves 31 and 44 may be replaced by a three-way valve (i.e. a valve making it possible via a "Y" connexion to connect the tubings Tub1 or Tub2 respectively to the circuit C3 or the circuit C4). If need be, the valve 44 is absent, and the stoppage of the pump 45 is sufficient to prevent a circulation of fluid through the purge circuit in so far as the pump is leak tight.

The invention claimed is:

1. An instrument for measuring the concentration of water isotopes in a gas sample loaded with water vapour, comprising:
   at least one inlet tubing for receiving a purge liquid or a calibration liquid;
   an analyser comprising:
     an inlet for receiving a gas sample loaded with water vapour;
     an analysis device for analysing said gas sample;
     an outlet for discharging said gas sample loaded with water vapour after the measurement by the analysis device;
     a connection circuit in normal measurement operation mode connecting the inlet to the outlet via said analysis device;
   a vaporiser comprising:
     at least one inlet connected to said inlet tubing;

a vaporising device for vaporising said purge liquid or said calibration liquid;

a circuit that connects to the analyser to transmit said vaporised calibration liquid to the analyser, said circuit that connects to the analyser connecting the inlet of the vaporiser to the outlet of the analyser via said analysis device;

an output circuit for discharging an overflow of said vaporised calibration liquid during measurement by the analyser, said output circuit being arranged such that the overflow is discharged without passing through the analyser;

a purge circuit that is different from the output circuit, the purge circuit being connected to the inlet of the vaporiser for sucking said vaporised purge liquid through the vaporiser during a purge operation, said purge circuit being arranged such that said vaporised purge liquid does not pass through the analyser, and a selector to provide two different flow circulations for the vaporised calibration liquid and the purge liquid through, respectively, the output circuit and the purge circuit so that the selector is configured to selectively establish:

a calibration operation state establishing the circulation of the calibration liquid through the circuit that connects to the analyser and the circulation of the overflow of the vaporised calibration liquid through the output circuit of the vaporiser;

a purge operation state establishing the circulation of the purge liquid through the purge circuit.

2. The instrument according to claim 1, wherein the circulation of the gas sample loaded with water vapour through the connection circuit of the analyser is established during said purge operation state.

3. The instrument according to claim 1, wherein said selector comprises a first valve in the output circuit of the vaporiser and a second valve in the purge circuit, the first valve being open in the calibration operation state and closed in the purge operation state, the second valve being open in the purge operation state and closed in the calibration operation state.

4. The instrument according to claim 3, wherein said first and second valves are electrically operated valves controlled by a control circuit.

5. The instrument according to claim 1, wherein the purge circuit comprises a pump.

6. The instrument according to claim 5, wherein the purge circuit comprises a desiccator upstream of the pump.

7. The instrument according to claim 5, wherein the second valve is arranged upstream of the pump.

8. The instrument according to claim 1, wherein an escape of the vaporised calibration liquid from the output circuit takes place to the open air.

9. The instrument according to claim 1, further comprising two inlet tubings, each being adapted to receive a purge liquid or a calibration liquid, said vaporiser comprising two inlets connected respectively to one of said inlet tubings.

10. The instrument according to claim 1, further comprising software means to remotely or automatically control said selector for selectively establishing said calibration operation state and said purge operation state.

11. The instrument according to claim 1, wherein the analysis device is an infrared absorption spectrometer.

* * * * *